(12) United States Patent
Sakamoto et al.

(10) Patent No.: US 7,534,928 B2
(45) Date of Patent: May 19, 2009

(54) TOPSHEET FOR ABSORBENT ARTICLE

(75) Inventors: Noriko Sakamoto, Tochigi (JP); Hiroko Sugiura, Tochigi (JP); Yasuo Toyoshima, Tochigi (JP); Shoichi Taneichi, Tochigi (JP); Wataru Saka, Tochigi (JP)

(73) Assignee: Kao Corporation, Tokyo (JP)

( * ) Notice: Subject to any disclaimer, the term of this patent is extended or adjusted under 35 U.S.C. 154(b) by 256 days.

(21) Appl. No.: 10/214,719

(22) Filed: Aug. 9, 2002

(65) Prior Publication Data
US 2003/0050615 A1    Mar. 13, 2003

(30) Foreign Application Priority Data
Aug. 10, 2001   (JP) ............................. 2001-244776

(51) Int. Cl.
*A61F 13/15*   (2006.01)

(52) U.S. Cl. ................. 604/378; 604/379; 604/380; 604/383

(58) Field of Classification Search ............ 604/385.01, 604/378, 379, 380, 383; 428/131–140, 170–172
See application file for complete search history.

(56) References Cited

U.S. PATENT DOCUMENTS

| | | | |
|---|---|---|---|
| 4,041,203 A | 8/1977 | Brock et al. | |
| 4,323,068 A | 4/1982 | Aziz | |
| 4,551,378 A | 11/1985 | Carey, Jr. | |
| 4,720,415 A | 1/1988 | Vander Wielen et al. | |
| 4,935,022 A | 6/1990 | Lash et al. | |
| 5,143,779 A | 9/1992 | Newkirk et al. | |
| 5,229,191 A | 7/1993 | Austin | |
| 5,348,547 A | 9/1994 | Payne et al. | |
| 5,399,174 A | 3/1995 | Yeo et al. | |
| 5,491,016 A | 2/1996 | Kaiser et al. | |
| 5,536,555 A | 7/1996 | Zelazoski et al. | |
| 5,591,149 A | 1/1997 | Cree et al. | |
| 5,612,118 A | 3/1997 | Schleinz et al. | |
| 5,817,394 A | 10/1998 | Alikhan et al. | |
| 5,989,688 A | 11/1999 | Barge et al. | |
| 6,362,391 B1 | 3/2002 | Mizutani et al. | |
| 6,673,418 B1 | 1/2004 | DeOlivera et al. | |
| 2002/0068150 A1 | 6/2002 | Taneichi et al. | |
| 2003/0134094 A1 | 7/2003 | Zafiroglu et al. | |
| 2003/0162460 A1 | 8/2003 | Saka et al. | |

FOREIGN PATENT DOCUMENTS

| | | | |
|---|---|---|---|
| CN | 1178101 A | 4/1998 |
| EP | 0327317 A2 | 8/1989 |
| EP | 359501 A2 | 3/1990 |
| EP | 0604731 A1 | 7/1994 |
| EP | 0841156 A1 | 5/1998 |
| EP | 1338262 A1 | 8/2003 |

(Continued)

*Primary Examiner*—Jacqueline F. Stephens
(74) *Attorney, Agent, or Firm*—Birch, Stewart, Kolasch & Birch, LLP

(57) ABSTRACT

A topsheet for absorbent articles is disclosed. The topsheet is used on the side of an absorbent article to be brought into contact with a wearer's body. The topsheet has an air permeability of 10 ml/cm$^2$·sec or more in the horizontal direction under a pressure of 10 cN/cm$^2$. The topsheet also has an air permeability of 10 to 500 ml/cm$^2$·sec in the horizontal direction under a pressure of 50 cN/cm$^2$.

7 Claims, 4 Drawing Sheets

FOREIGN PATENT DOCUMENTS

| | | | |
|---|---|---|---|
| GB | 2288412 A | 10/1995 |
| JP | 51-146584 A | 12/1976 |
| JP | 61-124667 A | 6/1986 |
| JP | 62-141167 | 6/1987 |
| JP | 63-296936 A | 12/1988 |
| JP | 63-309657 A | 12/1988 |
| JP | 2-133641 A | 5/1990 |
| JP | 02-300365 A | 12/1990 |
| JP | 04-312431 A | 11/1992 |
| JP | 5-25763 A | 2/1993 |
| JP | 6017356 A | 1/1994 |
| JP | 6-128853 | 5/1994 |
| JP | 7-232409 A | 9/1995 |
| JP | 8-3850 A | 1/1996 |
| JP | 9-003755 | 1/1997 |
| JP | 9-111631 | 4/1997 |
| JP | 09-117982 A | 5/1997 |
| JP | 10-80445 A | 3/1998 |
| JP | 2000-135239 | 5/2000 |
| JP | 2000-210334 A | 8/2000 |
| JP | 3131557 B2 | 11/2000 |
| JP | 2001-37805 A | 2/2001 |
| JP | 3181195 | 4/2001 |
| JP | 3181195 B2 | 4/2001 |
| JP | 2001-140158 A | 5/2001 |
| WO | WO 98/24389 * | 6/1998 |
| WO | WO00/35503 A1 | 6/2000 |

* cited by examiner

TOPSHEET FOR ABSORBENT ARTICLE

The present invention relates to a topsheet for absorbent articles, such as disposable diapers, sanitary napkins, and incontinence pads, which is to be brought into direct contact with a wearer's body.

BACKGROUND OF THE INVENTION

Topsheets used in absorbent articles, such as disposable diapers and sanitary napkins, are required to have not only absorption characteristics such that liquid body waste, e.g., urine or menstrual blood, is smoothly transferred to an underlying absorbent member but surface characteristics for not causing discomfort and skin troubles, such as an itch and a rash, due to overhydration.

Various kinds of topsheets of the type having an uneven surface on the wearer's side have hitherto been proposed. Most of the shapes of the unevenness of this type of topsheets are designed aiming at improvement on the above-mentioned absorption characteristics or improvement on feels such as softness to the touch, and conventional topsheets still have room for improvement to eliminate discomfort or skin troubles due to overhydration.

JP-A-9-111631 discloses wrinkled nonwoven fabric with a great number of streaky wrinkles arrayed on its surface, which is used as a topsheet of an absorbent article. However, the wrinkled nonwoven fabric is deformed easily in the thickness direction under pressure applied while worn, and the gaps between wrinkles are easily collapsed to lose breathability, which can cause discomfort or skin troubles due to overhydration.

JP-A-2000-135239 discloses an absorbent article, such as a sanitary napkin, in which a liquid-permeable nonwoven fabric sheet forming a large number of ridges is used as a topsheet to be brought into contact with the wearer's skin. Japanese Patent 3181195 discloses nonwoven fabric useful as a female component of a mechanical fastener system used, e.g., in disposable diapers, which fabric is composed of a first fiber layer and a second fiber layer partially joined together by thermal fusion, either one of the first and second fiber layers being thermally shrunken to raise the other to form regular projections.

The ridges described in JP-A-2000-135239 are easy to crush by the pressure while in use, impairing the permeability during wearing an absorbent article.

Having a large number of very fine bosses and depressions which are apt to make a hard material, the nonwoven fabric described in Japanese Patent 3181195 impairs the feel of touch during wearing and is not designed for suppressing discomfort or skin troubles due to overhydration. Therefore, the nonwoven fabric of Japanese Patent 3181195 is difficult to use as a topsheet of an absorbent article.

SUMMARY OF THE INVENTION

An object of the present invention is to provide a topsheet for absorbent articles which hardly causes overhydration while an absorbent article having the same is worn and thereby suppresses discomfort or skin troubles, such as an itch and a rash, due to overhydration.

The present invention accomplishes the above object by providing a topsheet used on the side of an absorbent article to be brought into contact with a wearer's body, which has an air permeability of 10 ml/cm$^2$·sec or more in the horizontal direction under a pressure of 10 cN/cm$^2$.

The present invention accomplishes the above object by providing a topsheet for absorbent articles used on the side of an absorbent article to be brought into contact with a wearer's body, which has a first fiber layer and a second fiber layer both comprising a fiber aggregate, the first fiber layer and the second fiber layer being partially thermally fusion-bonded together to form fusion-bonded joints in a prescribed pattern, the first fiber layer forming protrusions in portions other than the fusion-bonded joints, and the ratio of the substantial thickness of the protrusions to the thickness of the fusion-bonded joints being 5 to 50.

BRIEF DESCRIPTION OF THE DRAWINGS

The present invention will be more particularly described with reference to the accompanying drawings, in which.

DETAILED DESCRIPTION OF THE PREFERRED EMBODIMENTS

The present invention will be described in greater detail with reference to its preferred embodiments.

The topsheet according to the present invention is used on the side of an absorbent article which is to come into contact with a wearer's skin. Absorbent articles to which the topsheet of the present invention is applicable include disposable diapers, sanitary napkins, incontinence pads, and panty liners, which have, for example, a liquid permeable topsheet, a liquid impermeable backsheet, and an absorbent member interposed therebetween and are designed to absorb and retain body waste, such as urine and blood, in the absorbent member through the topsheet.

The topsheet according to the present invention is characterized by maintaining air permeability in its horizontal direction (every direction perpendicular to the thickness direction) (hereinafter referred to as a horizontal air permeability) even under a prescribed pressure. Specifically, the topsheet has a horizontal air permeability of 10 ml/cm$^2$·sec or more, preferably 50 to 800 ml/cm$^2$·sec, still preferably 100 to 500 ml/cm$^2$·sec, under a pressure of 10 cN/cm$^2$.

With such a horizontal air permeability under 10 cN/cm$^2$, overhydration during wearing an absorbent article is effectively prevented, to thereby securely prevent discomfort and skin troubles such as an itch and a rash due to overhydration. That is, even when the topsheet is pressed while in use by coming into intimate contact with a wearer's body, sufficient ventilation in the horizontal direction can be secured so that an increase of humidity in the atmosphere of the body to which an absorbent article is applied, due to waste discharging or perspiration, can be minimized to give the wearer comfort free from overhydration and skin rashes.

If the horizontal air permeability under 10 cN/cm$^2$ is less than 10 ml/cm$^2$·sec, poor ventilation in the horizontal direction (perpendicular to the thickness direction) results in a humidity rise due to waste discharging and perspiration, which can cause skin troubles such as an itch and a rash.

Although there is no particular upper limit of the horizontal air permeability under 10 cN/cm$^2$, the surface of the topsheet should be designed to keep contact with a wearer's body to such an extent as to avoid disadvantages such as liquid flow and leakage. From this viewpoint, the upper limit would be about 1000 ml/cm$^2$·sec.

Figure 1:
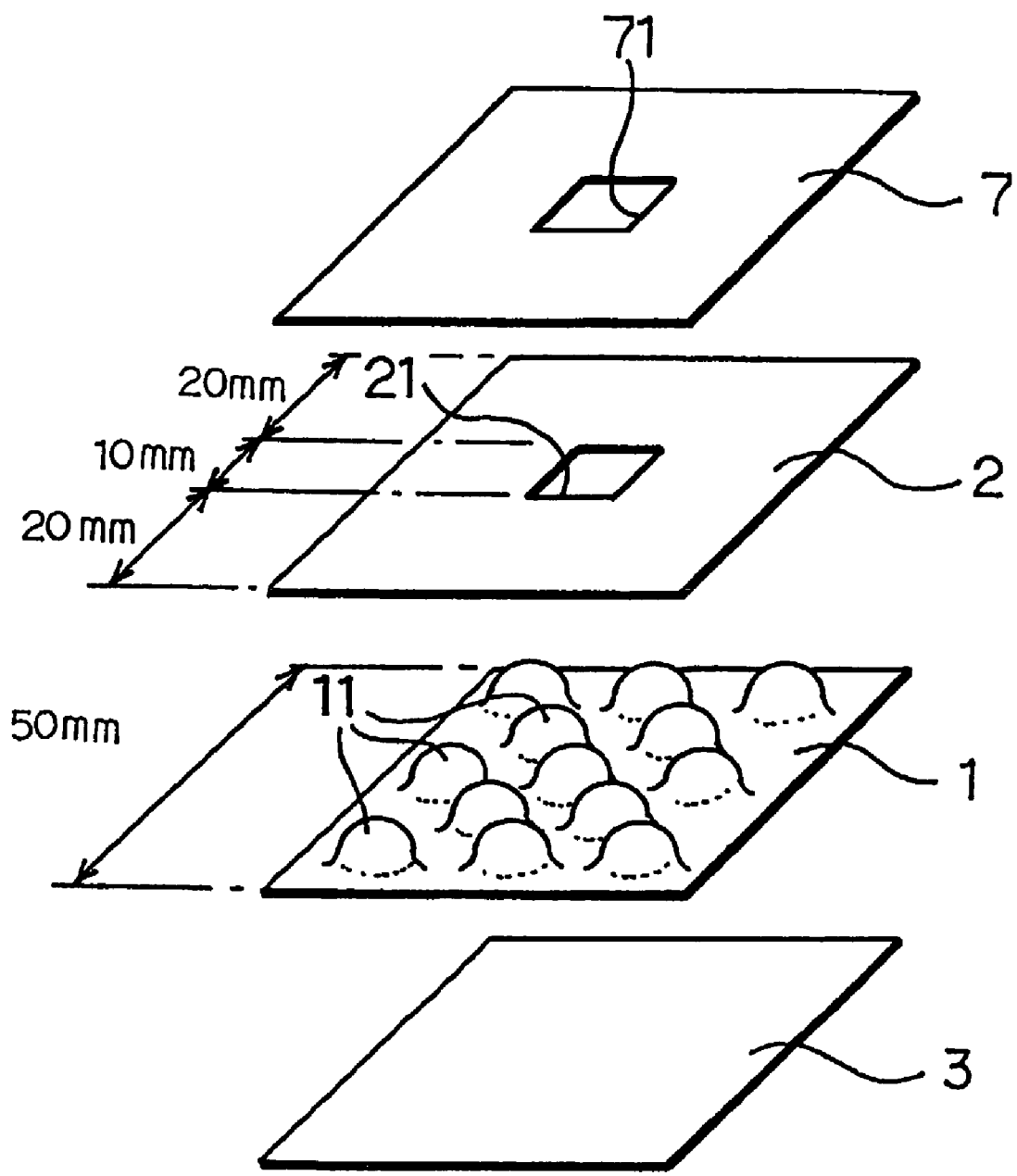
FIG. 1 is a perspective view illustrating the method of measuring an air permeability in the horizontal direction.
Figure 2:
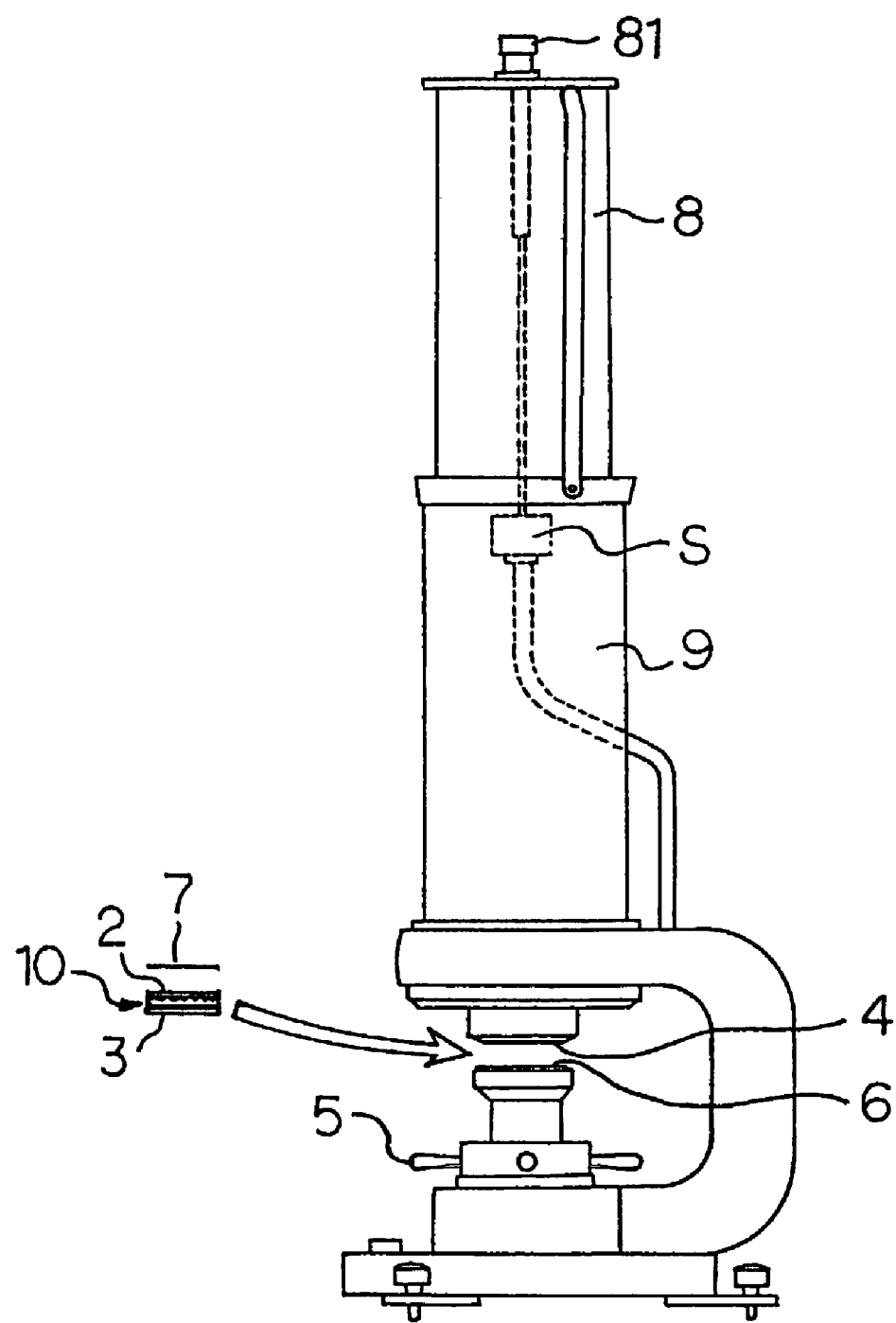
FIG. 2 is a schematic view of a Gurley tester used to measure an air permeability in the horizontal direction.

The horizontal air permeability under 10 cN/cm$^2$ can be measured as follows. At first, the thickness T1 of a topsheet under 10 cN/cm$^2$ load is measured. A square specimen 1 of 50 mm/side is cut out of the topsheet. As shown in FIG. 1, the specimen 1 is sandwiched between a 3 mm thick 50 mm-side square acrylic plate 2 having a 10 mm-side square opening 21 cut out of its central portion and a 3 mm thick 50 mm-side square acrylic plate 3, with the wearer's side of the specimen 1 (the side having protrusions 11) facing the acrylic plate 2. As shown in FIG. 2, the laminate 10 thus prepared is set under the gasket 4 of a Gurley tester Model B specified in JIS P8117 (Gurley method) with the acrylic plate 2 up, and the test specimen 1 is compressed to the thickness T1. The thickness of the specimen 1 is fixed at T1, and air is introduced into the central portion of the specimen 1 through the opening 21. The time required for introducing 300 ml of air is measured. The amount (ml) of air introduced per unit area (1 cm$^2$) of the opening 21 per second is calculated, which is taken as a horizontal air permeability under a pressure of 10 cN/cm$^2$.

The thickness T1 of the topsheet at 10 cN/cm$^2$ can be measured with a KES compression tester (e.g., Model KES-FB3, supplied by Katotec). A KES compression tester has an indenter and a receiver, between which a specimen is sandwiched and compression deformed in the thickness direction at a constant rate. A specimen with a greater size than the indenter is cut out of a topsheet and set on the receiver. The indenter is moved down at a speed of 1.2 mm/min to apply a compression load to a maximum of 50 cN/cm$^2$. The distance between the indenter and the receiver, which corresponds to the thickness of the specimen, and the load applied to the specimen are recorded until the compression load reaches to 50 cN/cm$^2$. The distance between the indenter and the receiver under a load of 10 cN/cm$^2$ is the T1 of the specimen.

A Gurley tester specified in JIS P8117 includes Gurley Densometer supplied by Kumagai Riki Kogyo K.K., which is shown in FIG. 2. Measurement of a horizontal air permeability with the equipment shown in FIG. 2 is carried out as follows. The laminate 10 is positioned under the gasket 4 with the acrylic plate 2 up, and a clamping handle 5 is turned to adjust the clearance between the gasket 4 and the opposing surface 6 so that the specimen 1 may have the thickness T1. A silicone plate 7 (hardness: 50) having a square opening 71 of 10 mm side in the central portion thereof (see FIG. 1) is inserted between the gasket 4 and the acrylic plate 2 so that air introduced may not leak through any gap other than the four lateral edges of the specimen 1.

An inner cylinder 8 is lifted by its knob 81 to thereby cause outer air to be sucked into an outer cylinder 9 and then let down into the outer cylinder 9. Thus, 300 ml of air is introduced from an air feed opening (not shown) at the center of the lower side of the gasket 4 into the center of the upper side of the specimen 1. The pressure of air introduction depends on the standardized weight of the inner cylinder 8. The time required for 300 ml of air to be introduced is measured, and the horizontal air permeability under 10 cN/cm$^2$ load is calculated. Symbol S is a photosensor having a combination of a projector and a receptor. A strip with slits which is attached to the inner cylinder passes between the projector and the receptor downward to provide signals to a digital counter, where the time is digitally displayed.

It is preferred for the topsheet according to the present invention to have a horizontal air permeability of 10 to 500 ml/cm$^2$·sec, particularly 20 to 200 ml/cm$^2$·sec, under a pressure of 50 cN/cm$^2$. Where the topsheet has a horizontal air permeability of 10 ml/cm$^2$·sec or more under 50 cN/cm$^2$, sufficient ventilation in the horizontal direction is maintained to ensure prevention of discomfort and skin troubles such as an itch and a rash due to overhydration even when an absorbent article is considerably pressed onto a wearer's body to bring the topsheet into intimate contact with the wearer's skin. With the topsheet having the horizontal air permeability under 50 cN/cm$^2$ of not more than 500 ml/cm$^2$·sec, an absorbent article gives little unpleasant feel of foreign matter, and reduction of absorbing performance such as liquid flow on the sheet surface can be prevented.

The horizontal air permeability under a pressure of 50 cN/cm$^2$ can be measured in the same manner as described above for measuring the horizontal air permeability under 10 cN/cm$^2$, except that the thickness T2 of a topsheet under 50 cN/cm$^2$ is previously measured and that air is introduced to the specimen 1 the thickness of which is fixed at T2.

It is preferred that the difference of the horizontal air permeability under 10 cN/cm$^2$ between the machine direction (MD) and the cross direction (CD) be small. Specifically, the MD to CD ratio of the horizontal air permeability under 10 cN/cm$^2$ is preferably 0.6 to 1.7, still preferably 0.8 to 1.5, particularly preferably 0.9 to 1.2. The MD/CD ratio of air permeability falling within the range 0.6 to 1.7, good ventilation is always secured against any movement or posture made by a wearer to provide a comfortable application atmosphere with little overhydration.

In case the MD and the CD of a sheet are indistinguishable, the longitudinal direction of the sheet is taken as the MD, and the width direction as the CD. In case the longitudinal direction and the width direction, still less the MD and the CD are indistinguishable, either one of two directions crossing at right angles is regarded as the MD, and the other as the CD.

The MD and CD air permeability under 10 cN/cm$^2$ can be measured in the same manner as for the horizontal air permeability under 10 cN/cm$^2$, except that two opposing side edges of the laminate 10 (the specimen 1 sandwiched in between the acrylic plates 2 and 3) are sealed with clay, etc. to prevent air leaks through these sides. For example, in measuring the MD air permeability, two opposing sides parallel in the MD are sealed, and vise versa.

In order to assure improved horizontal air permeability, it is preferred that the thickness of the topsheet under a pressure of 10 cN/cm$^2$ (T1) be 0.5 to 5 mm, particularly 0.8 to 4 mm and that under a pressure of 50 cN/cm$^2$ (T2) be 0.3 to 4 mm, particularly 0.5 to 3 mm.

Figure 3:
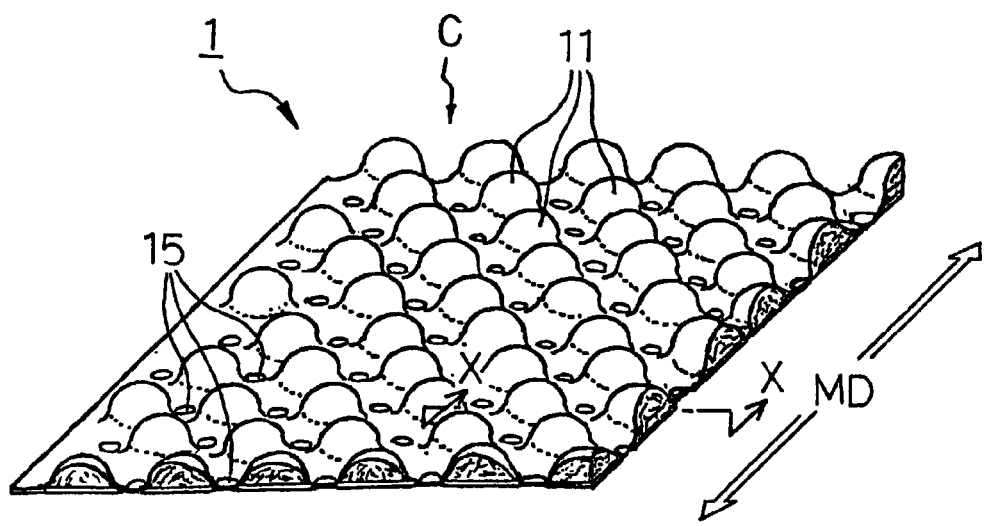
FIG. 3 is a perspective view showing an embodiment of the topsheet according to the present invention.
Figure 4:
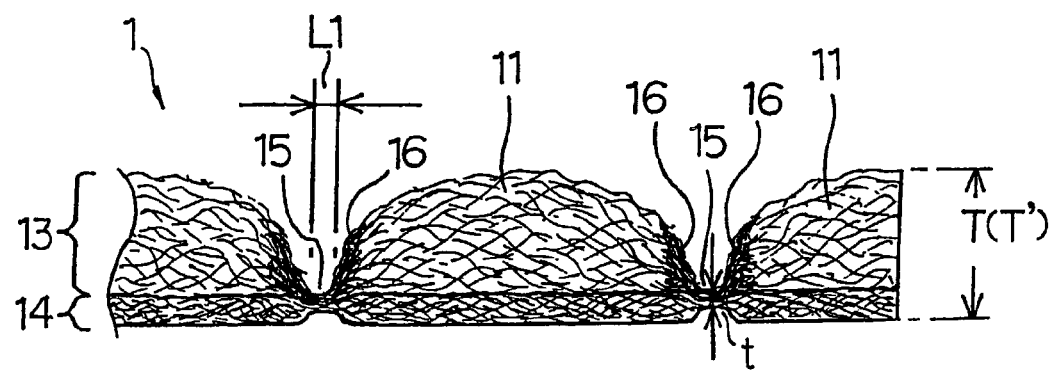
FIG. 4 is a cross-sectional view taken along X-X of FIG. 3.

FIGS. 3 and 4 illustrate a concrete structure of the topsheet for absorbent articles according to a preferred embodiment of the invention. The topsheet 1 shown in FIGS. 3 and 4 has a great number of protrusions 11 on the side C facing a wearer's skin, the protrusions 11 being discontinuous in the MD and CD. Each protrusion has substantially the same length in the MD and the CD (MD length/CD length is about 1/2 to 2/1).

The topsheet 1 preferably has a thickness T (see FIG. 4) of 0.5 to 10 mm, particularly 1 to 5 mm, and the shortest distance L1 (see FIG. 4) between adjacent protrusions 11 is preferably 0.5 to 15 mm, particularly 1 to 10 mm.

A combination of the topsheet thickness T of 0.5 mm or greater and the shortest distance L1 of 1 mm or greater provides large continuous depressions between protrusions 11 enough for allowing air to pass through thereby securing good and easy ventilation in the horizontal direction under pressure. With the topsheet thickness T being not more than 10 mm, the topsheet has a comfortable texture (softness, etc.) with a reduced feel of something foreign. With the shortest distance L1 being not more than 15 mm, a requisite minimum contact area with the wearer's skin is secured to retain absorbing performance while guaranteeing sufficient horizontal air permeability under pressure.

The thickness T of the topsheet 1 is measured as the thickness of the topsheet measured with the aforementioned KES compression tester under an initial pressure of 0.5 cN/cm$^2$.

The topsheet 1 according to the embodiment shown in FIG. 4 is made up of a first fiber layer 13 and a second fiber layer 14 both of which comprise a fiber aggregate.

The first fiber layer 13 and the second fiber layer 14 are superposed on each other and partially thermally fusion-bonded by heat embossing in a prescribed pattern. Fiber aggregates as the first and second fiber layers are superposed on each other, and an embossing surface (e.g., the peripheral surface of an embossing roll) with a large number of standing pins arrayed regularly is applied onto the first fiber layer side, whereby the fibers constituting the first fiber layer 13 and/or the fibers constituting the second fiber layer 14 are fusion bonded at the parts pressed and heated by the pins to form fusion-bonded joints 15.

After heat embossing, the second fiber layer 14 is shrunken in the horizontal direction to make the first fiber layer 13 form a large number of protrusions 11 in the parts other than the joints 15.

Because heat of heat embossing is applied to not only the parts of the first fiber layer 13 where the tips of the pins are pressed on to form the fusion-bonded joints 15 but the parts of the first fiber layer 13 which adjoin the fusion-bonded joints 15 (hereinafter referred to as joint-adjoining portions 16), fibers constituting the joint-adjoining portions 16 of the first fiber layer 13 around the fusion-bonded joints 15 are also fusion bonded among themselves. As a result, the joint-adjoining portions 16 of the protrusions 11, which are formed upon shrinkage of the second fiber layer 14, are denser and stiffer than other portions of the protrusions 11 which are nearer to their apices.

With the increased stiffness of the joint-adjoining portions 16, the protrusions 11 exhibit improved shape retention and are hardly collapsed to extend themselves over the fusion-bonded joints 15, thereby securing good and stable ventilation. It is possible to adopt other methods, such as ultrasonic sealing, for making the joint-adjoining portions 16 denser.

In order to make the joint-adjoining portions 16 denser and stiffer, the ratio of the substantial thickness T' of the protrusions 11 to the thickness t of the fusion-bonded joints 15 (T'/t) is preferably 5 to 50, particularly 8 to 30.

The substantial thickness T' of the protrusions 11 is the total thickness of the first fiber layer 13 and the second fiber layer 14. Where there is a space between the first fiber layer 13 and the second fiber layer 14, the substantial thickness T' is the total of the thickness of the first fiber layer 13 and that of the second fiber layer 14 as separately measured at a position with the maximum height corresponding to the apex of the protrusion 11. Where the first fiber layer 13 and the second fiber layer 14 are in contact in the protrusions 11, the substantial thickness T' is the thickness of the topsheet measured at a position having the maximum height corresponding to the apex of the protrusion 11. In this case, the substantial thickness T' of the protrusions is virtually the same as the above-identified topsheet thickness T under a pressure of 0.5 cN/cm$^2$, and the thickness T of the topsheet can be used in place of the substantial thickness T'.

The thickness t of the fusion-bonded joints 15 and the substantial thickness T' of the protrusions are measured from a cross-sectional photograph or image of the topsheet with no pressure applied. In this particular embodiment, a sample sheet was cut along a line passing the apices of the bulges and the fusion-bonded joints, and the cut area was observed with a digital microscope VH-8000 from Keyence to measure the thicknesses t and T'.

The denseness of the joint-adjoining portions 16 can be improved to increase the stiffness by controlling the thickness t of the fusion-bonded joints 15 with respect to the substantial thickness T' of the protrusions. From this viewpoint, the thickness t of the fusion-bonded joints 15 is desirably 0.01 to 1 mm, more desirably 0.1 to 0.5 mm, in the present embodiment.

When viewed from above, the fusion-bonded joints 15 are circular, and a large number of circular fusion-bonded joints 15 are almost equally spaced in a regular configuration. The first fiber layer 13 bulges upward in the areas surrounded by four fusion-bonded joints 15 to form a great number of protrusions 11. Each protrusion 11 is dome-shaped and filled with the fibers making the first fiber layer 13.

The first fiber layer 13 and the second fiber layer 14 differ from each other in kind and/or formulation of constituent fibers. Both the first fiber layer 13 and the second fiber layer 14 comprising a fiber aggregate, the topsheet 1 as a whole exhibits ventilation in its thickness direction.

To assure improved air permeability in the horizontal direction, a preferred number of pins of the embossing surface (e.g., the peripheral surface of the embossing roll) with which fusion-bonded joints are formed is 1 to 15, particularly 3 to 10, per cm$^2$. To assure absorption performance as well as improved horizontal air permeability, a preferred number of fusion-bonded joints 15 after thermal shrinkage is 1 to 30, particularly 5 to 20, per cm$^2$ of the topsheet.

Fibers suitable to constitute the first fiber layer include fiber of thermoplastic polymers, such as polyolefins, e.g., polyethylene and polypropylene, polyesters, e.g., polyethylene terephthalate, and polyamides. Core/sheath type conjugate fiber or side-by-side conjugate fiber made up of these thermoplastic polymers are also useful. It is preferred for the fiber constituting the first fiber layer 13 to have substantially no thermal shrinkability or to have no shrinkability below the thermal shrinkage temperature of the fiber constituting the second fiber layer 14 hereinafter described.

Thermally shrinkable fiber made of a thermoplastic polymer id suitably used to constitute the second fiber layer. It is also preferred for the fiber to exhibit elastomeric behavior. Such fiber includes self-crimping fiber. Self-crimping fiber before being crimped can be handled in the same manner as with ordinary fibers used for nonwoven fabrics and, upon being heated at a prescribed temperature, shrinks in a helix. Self-crimping fiber includes eccentric core/sheath type or side-by-side type conjugate fiber composed of two kinds of thermoplastic polymers having different percent shrinkages. Examples of useful self-crimping fiber are described in JP-A-9-296325 and Japanese Patent 2759331. The second fiber layer can comprise such self-crimping fiber so that it may shrink with self-crimping of the fiber.

The first and second fiber layers can additionally comprise other fibers, such as absorbent fibers, e.g., rayon, cotton, and hydrophilized acrylic fiber.

The fiber aggregate as the first fiber layer includes a web formed by carding and a composite material composed of such a web and nonwoven fabric fabricated by various methods.

The fiber aggregate as the second fiber layer includes (1) a web containing self-crimping fiber and formed by carding, (2) thermally shrinkable nonwoven fabrics (nonwoven fabrics capable of shrinking on heating to a prescribed temperature) prepared by thermal fusion bonding, water needling, needle punching, solvent adhesion, spun bonding, or melt-blowing, and (3) a thermally shrinkable net.

It is desirable for the first fiber layer 13 to have a basis weight of 5 to 60 g/m$^2$, particularly 10 to 40 g/m$^2$, to form protrusions with sufficient height thereby to ensure horizontal ventilation. It is desirable for the second fiber layer 14 to have a basis weight of 5 to 50 g/m$^2$, particularly 10 to 30 g/m$^2$, to develop sufficient thermal shrinkability thereby to make the first fiber layer protrude without impairing absorbing performance of the topsheet. The term "basis weight" as referred to here is the basis weight of the respective fiber layers before being bonded.

With respect to the basis weight after thermal shrinkage to form bulges, it is desirable for the first fiber layer 13 to have a basis weight of 10 to 90 g/m$^2$, particularly 20 to 80 g/m$^2$, for improving horizontal air permeability and bulge forming properties.

The topsheet 1 according to the present invention preferably has a basis weight of 15 to 200 g/m$^2$, particularly 30 to 150 g/m$^2$, from the standpoint of horizontal air permeability, protrusion shape retention, absorption performance, and the like.

The topsheet 1 may have a large number of perforations. For example, the first and/or the second fiber layers of the present embodiment preferably have perforations of 0.2 to 10 mm in diameter. Such perforations assist body fluids, such as urine, blood, and soft stools, to pass through the topsheet 1, which ensures leakproofness and reduction of overhydration.

The present invention is not limited to the above-described embodiments. For example, a third fiber layer that may be the same or different from the first fiber layer can be provided on the second fiber layer 14 on the side opposite to the first fiber layer side. The topsheet may have a single layer structure comprising a fiber aggregate.

Further, the topsheet may have a single or multiple layer structure made of any other materials that are substantially permeable to air, such as air-permeable films, perforated films, nets, composite materials composed of two or more thereof, and composite materials composed of two or more thereof and a fiber aggregate.

The present invention will now be illustrated in greater detail with reference to Examples. The following Examples are presented as being exemplary of the present invention and should not be considered as limiting.

EXAMPLE 1

(1) Preparation of First Fiber Layer

Core/sheath conjugate fiber NBF (SH) (available from Daiwabo Co., Ltd.; 2.2 dtex×51 mm; core: polyethylene terephthalate (PET); sheath: polyethylene (PE)) was carded into a web having a basis weight of 25 g/m$^2$, which was used as a first fiber layer.

(2) Preparation of Second Fiber Layer

Self-crimping fiber CPP (available from Daiwabo Co., Ltd.; 2.2 dtex×51 mm) was carded into a web having a basis weight of 25 g/m$^2$, which was used as a second fiber layer.

(3) Preparation of Topsheet

Figure 5:
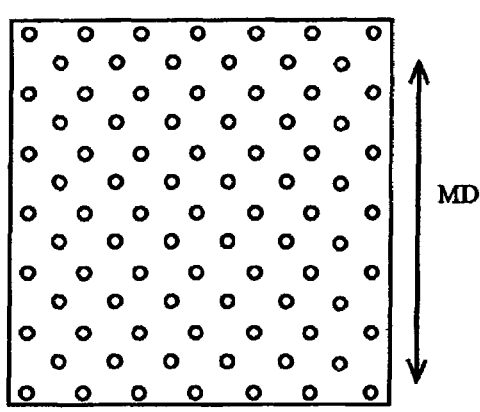
FIG. 5 is a plan view of the embossing pattern used in Example 1.

The first fiber layer and the second fiber layer were superposed on each other and joined in a prescribed pattern by heat embossing. Heat embossing was carried out by pressing an embossing roll onto the first fiber layer side at 220° C. for 10 seconds. The embossing roll had a large number of pins regularly arranged on its surface in a pattern shown in FIG. 5. The pins each had a diameter of 1.5 mm and were spaced at a pitch of 6 mm.

The heat-bonded layers were left to stand in an electric drier set at 130° C. for 10 minutes to crimp the self-crimping fibers of the second fiber layer. As a result, the second fiber layer shrank, and the first fiber layer was raised in the portions other than the heat-bonded joints to obtain a topsheet for absorbent articles having a great number of protrusions shown in FIGS. 3 and 4.

The resulting topsheet had the thickness T under 0.5 cN/cm$^2$ load (the height of protrusions) of 3.1 mm. The shortest distance L1 between adjacent protrusions was 1 to 1.5 mm. The joint-adjoining portions of the individual protrusions were stiffer than the other portions due to thermal fusion of the sheath component of the core/sheath conjugate fiber.

EXAMPLE 2

Figure 6:
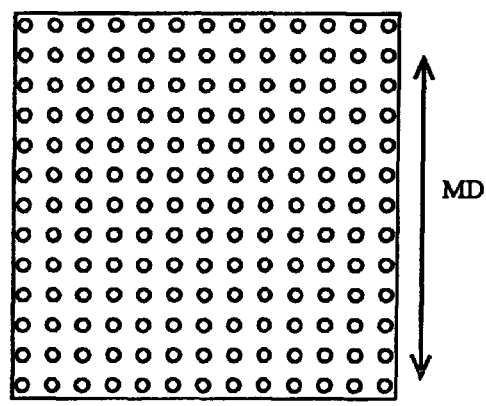
FIG. 6 is a plan view of the embossing pattern used in Example 2.

A topsheet for absorbent articles was prepared in the same manner as in Example 1, except for using the embossing pattern shown in FIG. 6.

The resulting topsheet had the thickness T under 0.5 cN/cm$^2$ load (the height of protrusions) of 2.3 mm. The shortest distance L1 between adjacent protrusions was 1 to 1.5 mm. The joint-adjoining portions of the individual protrusions were stiffer than the other portions due to thermal fusion of the core/sheath conjugate fibers.

COMPARATIVE EXAMPLES 1 AND 2

The topsheet used in a commercially available sanitary napkin Lorie Yawaraka Mesh, available from Kao Corp. and the topsheet used in a commercially available sanitary napkin Lorie Dry-up Mesh, available from Kao Corp. were prepared for comparison.

COMPARATIVE EXAMPLE 3

Core/sheath conjugate fiber available from Daiwabo Co., Ltd. (core: PET/sheath: PE=40/60 by volume; fineness: 2 denier) was carded into a nonwoven fabric sheet having a basis weight of 25 g/cm$^2$. A hot-melt adhesive was applied in 1 mm-wide stripes parallel to the MD at a pitch of 2 mm (at an interval of 1 mm).

The same nonwoven fabric sheet was pressed onto an embossing die having a 1 mm high 1 mm wide parallel ridges at a pitch of 2 mm (at a 1 mm interval) and deformed to have a square wavy form. The deformed sheet was bonded to the above-described nonwoven sheet via the hot-melt adhesive.

The resulting topsheet had a large number of 1 mm wide parallel projections at a 2 mm pitch. The joints of the two nonwoven fabric sheets were 1 mm wide. The topsheet had an apparent thickness (corresponding to the thickness T of the topsheet under a pressure of 0.5 cN/cm$^2$) of 0.9 mm, with the height of the projections from their foot being 0.7 mm.

COMPARATIVE EXAMPLE 4

A topsheet for absorbent articles was prepared in the same manner as in Example 1, except for using an embossing roll having pins with a diameter of 1 mm spaced at a pitch of 1 mm. The resulting topsheet had the thickness T under a pressure of 0.5 cN/cm² of 0.5 mm. The shortest distance L1 between adjacent protrusions was 0.7 mm.

Measurement of Air Permeability:

The horizontal air permeability under a pressure of 10 cN/cm² and 50 cN/cm² and the MD and the CD air permeabilities under a pressure of 10 cN/cm² of the topsheets prepared in Examples and Comparative Examples were measured according to the methods previously described. The results obtained are shown in Table 1 below.

Performance Evaluation (Measurement of Skin Conductance):

A 50 mm wide 75 mm long piece of the topsheet was given 6 g of water on its side intended to be brought into contact with a wearer's body and fixed on the inner side of a forearm of human volunteers with a bandage with the water-added side in contact with the skin. Two hours later, the skin conductance was measured. The difference from the skin conductance before the patch test was taken as a skin conductance increase. The results are also shown in Table 1. The skin conductance was measured with a skin surface hydrometer SKICON 200, supplied by IBS Co., Ltd.

TABLE 1

| | | | Example | | Comparative Example | | | |
|---|---|---|---|---|---|---|---|---|
| | | | 1 | 2 | 1 | 2 | 3 | 4 |
| Air Permeability (ml/cm² · sec) | 10 cN/cm² Load | Horizontal | 200.0 | 136.4 | 7.1 | 4.5 | 8.2 | 7.4 |
| | | MD | 157.9 | 100.0 | 6.3 | 4.4 | 6.9 | 6.5 |
| | | CD | 157.9 | 107.1 | 5.6 | 0.9 | 5.8 | 7.0 |
| | | MD/CD | 1.0 | 0.9 | 1.1 | 4.9 | 1.2 | 0.9 |
| | 50 cN/cm² Load; Horizontal | | 41.7 | 31.3 | 1.2 | 2.3 | 1.4 | 1.4 |
| Topsheet Thickness T under 0.5 cN/cm² Load (mm) | | | 3.1 | 2.3 | 0.9 | 0.6 | 0.9 | 0.9 |
| Substantial Thickness T of Protrusions (mm) (N = 3) | | | 3.1 | 2.3 | 0.4 | 0.2 | 0.35 | 0.9 |
| Shortest Distance L1 between Protrusions (mm) | | | 1-1.5 | 1-1.5 | — | — | 1.0 | 0.7 |
| Total Basis Weight of Topsheet (g/m²) | | | 114 | 99 | 25 | 27 | 104 | 76 |
| Basis Weight of 1st Fiber Layer after Protrusion Formation (g/m²) | | | 57 | 49 | — | — | 78 | 38 |
| Topsheet Thickness T1 under 10 cN/cm² Load (mm) | | | 2.5 | 1.7 | 0.48 | 0.47 | 0.80 | 0.70 |
| Topsheet Thickness T2 under 50 cN/cm² Load (mm) | | | 1.6 | 1.2 | 0.24 | 0.41 | 0.50 | 0.54 |
| Thickness t of Fusion-bonded Joints (mm) | | | 0.2 | 0.2 | — | — | 0.5 | 0.2 |
| T/t Ratio | | | 15.5 | 11.5 | — | — | 2.6 | 4.5 |
| Skin Conductance Increase | | | 389 | —* | 732 | 919 | —* | —* |

*Not measured.

The skin conductance increases by the topsheets according to the present invention are about a half of those of the comparative topsheets, proving that the topsheets of the present invention hardly cause overhydration.

Figure 7:
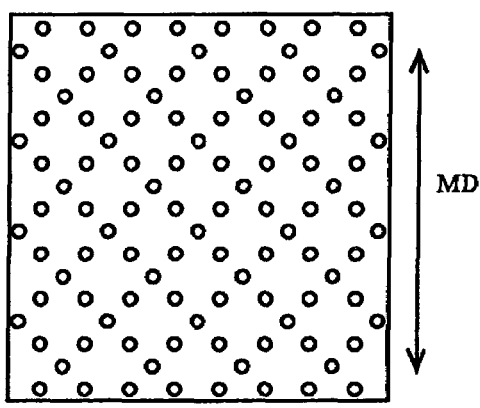
FIG. 7 is a plan view of another embossing pattern adoptable to the topsheet of the present invention.

The embossing pins used to produce the topsheet of the invention may have the configuration shown in FIG. 7.

The topsheet for absorbent articles according to the present invention hardly causes overhydration while an absorbent article having the topsheet is worn and thereby suppresses discomfort or skin troubles such as an itch and a rash due to overhydration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2001-244776 filed Aug. 10, 2001.

What is claimed is:

1. A topsheet for absorbent articles used on the side of an absorbent article to be brought into contact with a wearer's body, which has an air permeability of 100 to 500 ml/cm²·sec or more in the horizontal direction under a pressure of 10 cN/cm², with a ratio of the air permeability under 10 cN/cm² in the machine direction to that in the cross direction being 0.6 to 1.7, and which has a first fiber layer and a second fiber layer both comprising a fiber aggregate, said second fiber layer comprising thermally shrinkable fiber, said first fiber layer and said second fiber layer being partially thermally fusion-bonded together to form fusion-bonded joints in a prescribed pattern and a large number of the fusion-bonded joints are almost equally spaced in a regular configuration with the fusion-bonded joints having a thickness t of 0.1 to 0.5 mm, said first fiber layer forming protrusions in portions other than said fusion-bonded joints by the heat shrinkage of said thermally shrinkable fiber of said second fiber layer wherein each protrusion is dome-shaped and filled with the fibers making the first fiber layer, the portions of said protrusions adjoining said fusion-bonded joints being denser and stiffer than other portions of said protrusions, and the first fiber layer bulging upward in areas that are surrounded by fusion-bonded joints to form a great number of the protrusions, said second fiber layer being substantially flat in portions other than said fusion-bonded joints, and wherein a ratio of the substantial thickness T' of the protrusions to the thickness t of the fusion-bonded joints (T'/t) is 5 to 50.

2. The topsheet for absorbent articles according to claim 1, which has an air permeability of 10 to 500 ml/cm²·sec in the horizontal direction under a pressure of 50 cN/cm².

3. The topsheet for absorbent articles according to claim 2, which has an air permeability of 20 to 200 ml/cm²·sec in the horizontal direction under a pressure of 50 cN/cm².

4. The topsheet for absorbent articles according to claim 1, which has a great number of protrusions discontinuous in the longitudinal and width directions on the side facing a wearer's body, the topsheet under a pressure of 0.5 cN/cm² having a thickness of 0.5 to 10 mm, and the shortest distance between adjacent protrusions being 0.5 to 15 mm.

5. The topsheet for absorbent articles according to claim 1, wherein the number of fusion-bonded joints after thermal shrinkage is 1 to 30 per cm² of the topsheet.

6. A topsheet for absorbent articles used on the side of an absorbent article to be brought into contact with a wearer's body, which has a first fiber layer and a second fiber layer both comprising a fiber aggregate, said second fiber layer comprising thermally shrinkable fiber, said first fiber layer and said second fiber layer being partially thermally fusion-bonded together to form fusion-bonded joints in a prescribed pattern, said first fiber layer forming protrusions in portions other than said fusion-bonded joints by the heat shrinkage of said thermally shrinkable fiber of said second fiber layer, said second fiber layer being substantially flat in portions other than said fusion-bonded joints, and the ratio of the substantial thickness T' of said protrusions to the thickness t of said fusion-bonded joints (T'/t) is 5 to 50, wherein said protrusions are discontinuous in the MD and CD and each protrusion possesses a MD length/CD length ratio of about 1/2 to 2/1 and the shortest distance between adjacent protrusions is 0.5 to 15 mm, wherein the topsheet possesses an air permeability of 100 to 500 ml/cm²·sec or more in the horizontal direction under a pressure of 10 cN/cm² with a ratio of the air permeability under 10 cN/cm² in the MD to that in the CD being 0.6 to 1.7, and wherein the topsheet under a pressure of 0.5 cN/cm² has a thickness of 0.5 to 10 mm.

7. The topsheet for absorbent articles according to claim 6, wherein the number of fusion-bonded joints after thermal shrinkage is 1 to 30 per cm² of the topsheet.

* * * * *